(12) United States Patent
Samangooie

(10) Patent No.: US 9,022,679 B2
(45) Date of Patent: May 5, 2015

(54) TOUCH-FREE APPLICATOR

(71) Applicant: Casey Samangooie, Wadsworth, IL (US)

(72) Inventor: Casey Samangooie, Wadsworth, IL (US)

(73) Assignee: CaseMed Engineering, LLC, Wadsworth, IL (US)

( * ) Notice: Subject to any disclaimer, the term of this patent is extended or adjusted under 35 U.S.C. 154(b) by 277 days.

(21) Appl. No.: 13/660,521

(22) Filed: Oct. 25, 2012

(65) Prior Publication Data
US 2013/0343797 A1    Dec. 26, 2013

Related U.S. Application Data

(60) Provisional application No. 61/690,254, filed on Jun. 22, 2012.

(51) Int. Cl.
| | | |
|---|---|---|
| *B43K 5/14* | (2006.01) | |
| *A45D 40/26* | (2006.01) | |
| *A61F 13/40* | (2006.01) | |
| *A45D 37/00* | (2006.01) | |

(52) U.S. Cl.
CPC ............. *A45D 40/26* (2013.01); *A61M 35/006* (2013.01); *A45D 37/00* (2013.01); *A45D 2200/1018* (2013.01); *A45D 2200/1045* (2013.01)

(58) Field of Classification Search
CPC .................................................... A61M 35/006
USPC ...................... 401/132–134; 604/3
See application file for complete search history.

(56) References Cited

U.S. PATENT DOCUMENTS

| | | | | |
|---|---|---|---|---|
| 3,386,793 | A * | 6/1968 | Stanton | 401/132 |
| 3,466,131 | A | 9/1969 | Arcudi | |
| 3,986,640 | A * | 10/1976 | Redmond | 222/92 |
| 4,140,409 | A * | 2/1979 | DeVries | 401/132 |
| 4,430,013 | A * | 2/1984 | Kaufman | 401/132 |
| 4,475,835 | A * | 10/1984 | Verboom et al. | 401/132 |
| 4,893,956 | A | 1/1990 | Wojcik et al. | |
| 4,963,045 | A | 10/1990 | Willcox | |
| 5,775,826 | A | 7/1998 | Miller | |
| 6,425,701 | B1 | 7/2002 | Jacobs | |
| 7,264,414 | B2 | 9/2007 | Mcreynolds et al. | |
| 8,215,859 | B2 | 7/2012 | Kaufman et al. | |
| 8,425,136 | B2 * | 4/2013 | Littig et al. | 401/133 |
| 2002/0197094 | A1 * | 12/2002 | Gruenbacher et al. | 401/133 |
| 2006/0039742 | A1 | 2/2006 | Cable et al. | |
| 2007/0053737 | A1 * | 3/2007 | Morris et al. | 401/133 |
| 2007/0183836 | A1 * | 8/2007 | Lampe et al. | 401/134 |

FOREIGN PATENT DOCUMENTS

GB          1562640 A      3/1980

* cited by examiner

*Primary Examiner* — Jennifer C Chiang
(74) *Attorney, Agent, or Firm* — Lesley A. Wallerstein, LLC

(57) ABSTRACT

A unitary hand-held, single-use liquid dispenser and applicator is disclosed. A squeezable handle also serves as a reservoir for liquid. A non-forming thermoplastic film seals liquid within the reservoir. Novel weaknesses in the film can be broken on demand to create an opening for liquid to freely flow onto an absorbent pad. A user can thus dispense and apply the liquid without ever touching the liquid or the surface with his hands.

18 Claims, 9 Drawing Sheets

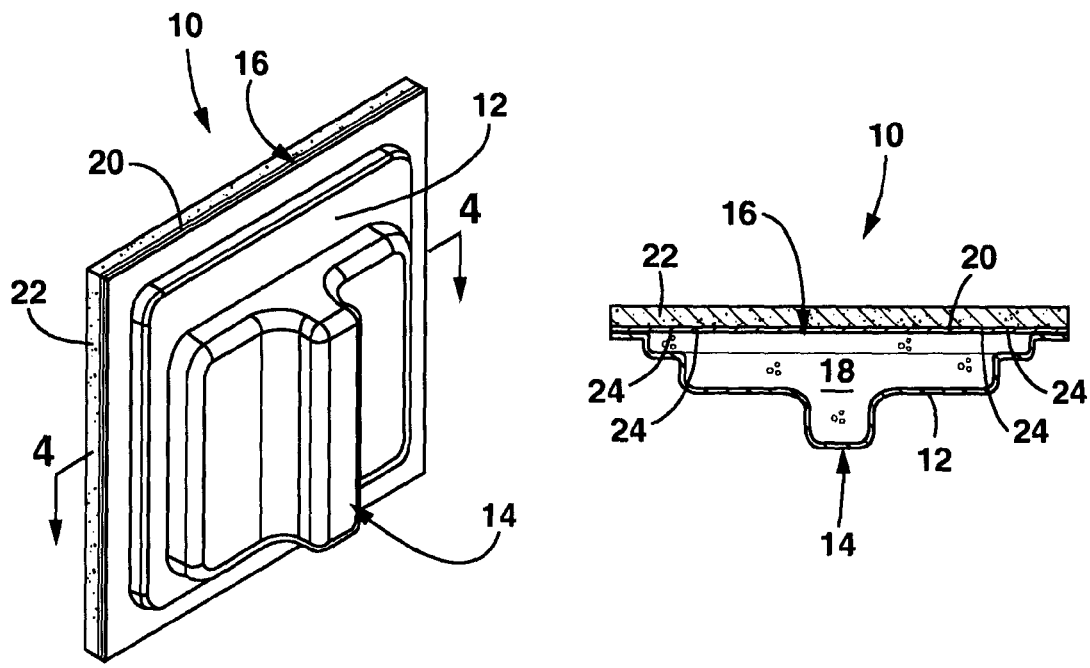
FIG. 3  FIG. 4
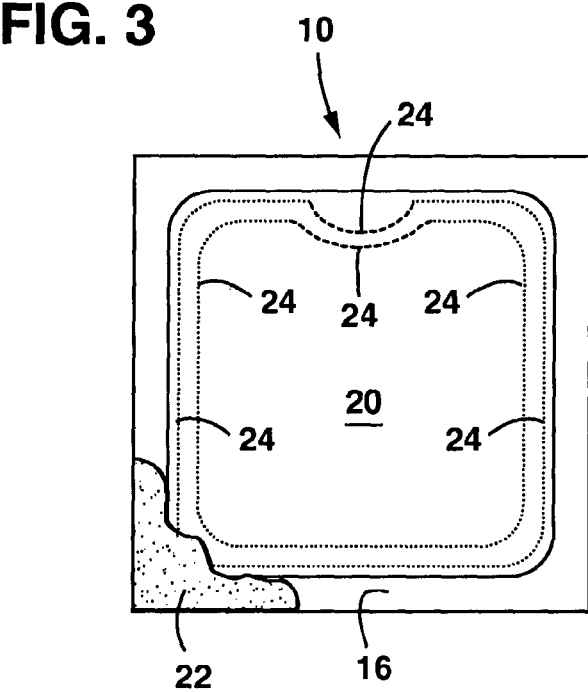
FIG. 5

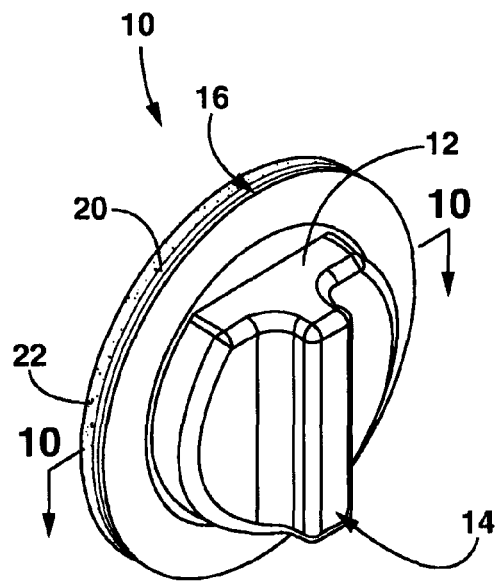
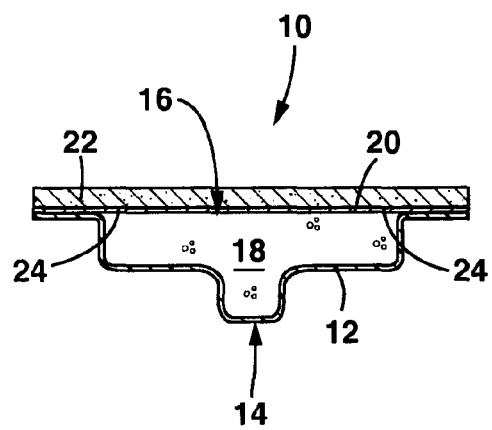
FIG. 9  FIG. 10
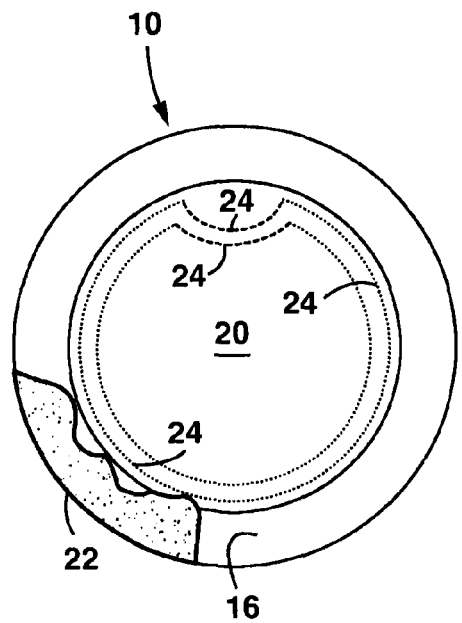
FIG. 11

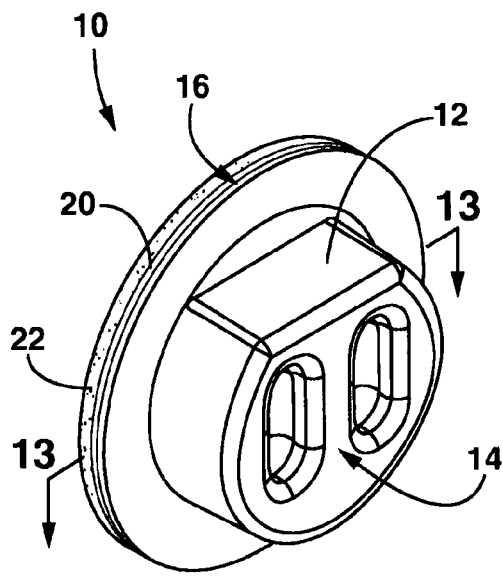
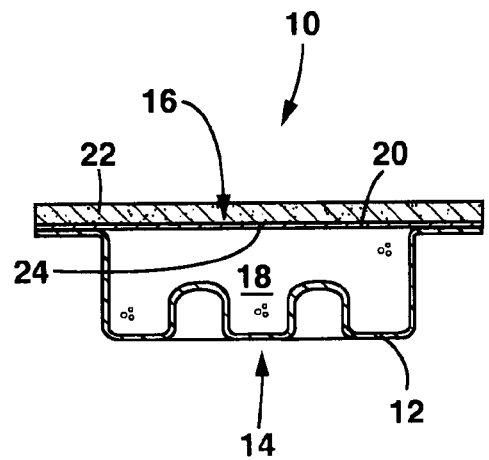
FIG. 12  FIG. 13
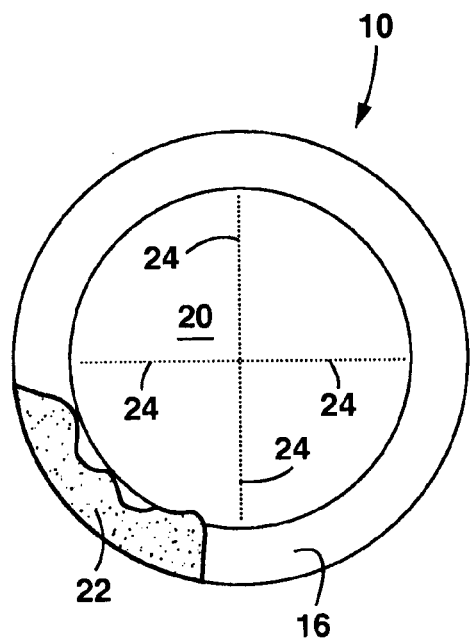
FIG. 14

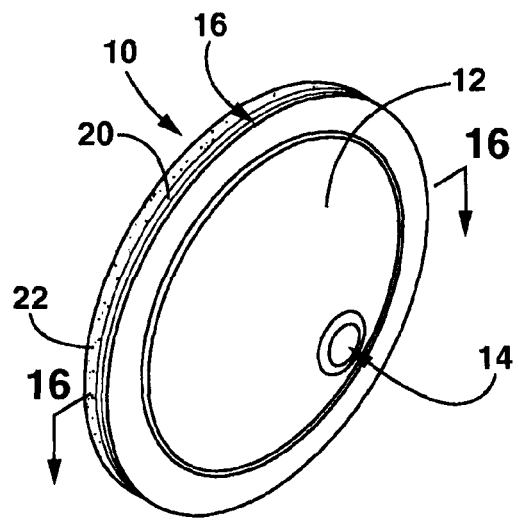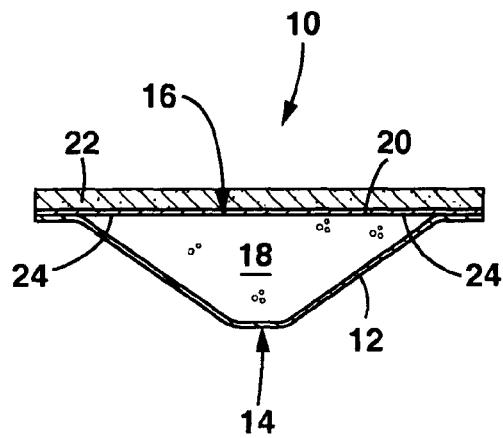
FIG. 15  FIG. 16
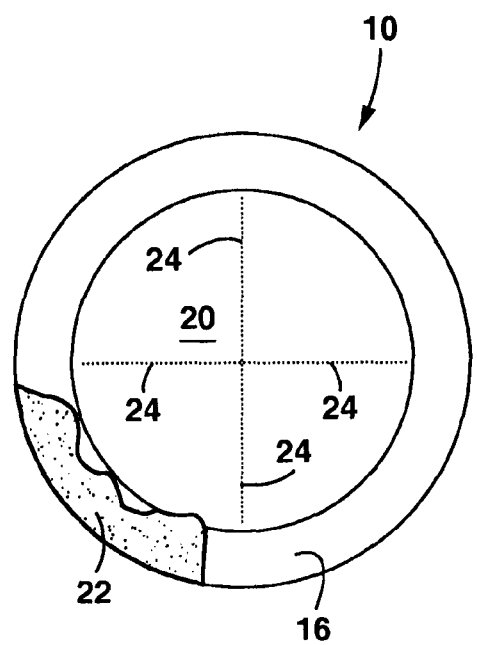
FIG. 17

TOUCH-FREE APPLICATOR

CROSS-REFERENCE TO RELATED APPLICATION

This application claims the benefit of U.S. Provisional Application No. 61/690,254, filed Jun. 22, 2012.

STATEMENT REGARDING FEDERALLY SPONSORED RESEARCH OR DEVELOPMENT (not applicable)

NAMES OF PARTIES TO A JOINT RESEARCH AGREEMENT (not applicable)

REFERENCE TO SEQUENCE LISTING, A TABLE OR A COMPUTER PROGRAM LISTING COMPACT DISC APPENDIX (not applicable)

FIELD OF THE INVENTION

This invention relates to hand held liquid applicators.

BACKGROUND OF THE INVENTION

In our increasingly mobile world, cars, trains and airplanes have become second homes and offices. It is becoming more and more necessary to carry life's necessities with us as we go. You can buy travel-size bottles of moisturizer, shaving cream, shoe polish, insect repellant, nail polish remover and antibacterial lotion at any grocery store. They fit discreetly in a purse, briefcase or makeup bag and are small enough to pass through airport security.

As convenient and portable as these packages are, they still remain potentially unsanitary. The user must ultimately touch the product as he applies it to the desired surface. This creates more mess and more potential for contamination. In the case of a medication, he might not know how much to apply.

The industry needs a travel-sized liquid container that is also an applicator. It should be portable for travel, small enough to pass through airport security, clean and sanitary. The container should securely hold a pre-measured amount of the liquid until it is needed. The container should fit comfortably in the palm of the hand, yet have a low profile. The liquid can be dispensed and applied on demand with a gentle squeezing or pinching motion. No liquid need ever touch the hands.

The container is adapted to hold, dispense and apply highly viscous liquids such as shoe polish, sun block or deodorant. It is equally suitable for containing low viscosity products like nail polish remover or rubbing alcohol. A traveler, backpacker or commuter could pack several of these in small spaces and be reassured he has what he needs for the day without being weighted down. Thus it is a container and an applicator all in one.

BRIEF SUMMARY OF THE INVENTION

In accordance with one embodiment of the invention, I provide a sanitary, hand-held, on demand, single-use combination liquid container and applicator. The applicator comprises four primary elements. The first is a reservoir-handle element defining a volume. The reservoir-handle element is sized for a palm of an average adult user. The reservoir-handle comprises a handle end bearing various surface details suggesting where to optimally position fingers or thumb for squeezing or pinching. Opposite the handle end is an open, dispensing end through which the liquid flows. The boundary of the handle end with the dispensing end defines a perimeter.

The second element comprises a film securely and permanently coupled to the perimeter of the dispensing end of the reservoir-handle. This film covers but does not extend beyond the entire perimeter of the opening of the dispensing end. The film may comprise either a single layer bound to the opening perimeter of the reservoir-handle and retaining the liquid therewithin.

The third element comprises a flat absorbent pad securely and permanently sealed to an opposing side of a non-forming thermoplastic film. The non-forming thermoplastic film is sealed to the pad along the same perimeter line as the seal between the film and the reservoir-handle element. The non-forming film is thereby sandwiched between the reservoir-handle and the pad. The pad may or may not extend beyond the dimensions of the perimeter of the opening of the reservoir-handle.

This film bears novel weaknesses which the user can break on demand. These weaknesses are created intentionally so that squeezing the handle with sufficient force dispenses the liquid from the reservoir-handle and breaks the weaknesses, forming an opening. The configuration and position of these film weaknesses determine the size of this opening. The advantage of dispensing liquid through this system is that the film is strong enough to retain the liquid in a pre-measured and sanitary condition while in transport or storage, yet weak enough to be broken by the squeeze of a finger and thumb. Thus it is both clean and convenient. The configuration and pattern of the weaknesses can vary depending on the viscosity of the liquid and the degree of control desired in dispensing the liquid. Very viscous liquids can pass through a larger hole onto the absorbent pad. A user can thus apply the liquid without ever touching the liquid with his hands.

The reservoir-handle comprises a material which is resilient enough to hold its own shape at room temperature, yet soft enough to be squeezed or pinched by a user of average strength. This material should not absorb the liquid inside. Preferably the material is not permeable to water.

AMENDMENTS TO THE BRIEF DESCRIPTION OF THE SEVERAL VIEWS OF THE DRAWINGS

FIG. 3 is a perspective view of a second embodiment of the invention.

FIG. 4 is a center section view taken from FIG. 3.

FIG. 5 is a bottom view of FIG. 3 with the reservoir-handle and film cut away.

FIG. 9 is a perspective view of a fourth embodiment.

FIG. 10 is a center section view taken from FIG. 9.

FIG. 11 is a bottom view of FIG. 9 with the reservoir-handle and film cut away.

FIG. 12 is a perspective view of a fifth embodiment.

FIG. 13 is a center section view taken from FIG. 12.

FIG. 14 is a bottom view of FIG. 12 with the reservoir-handle and film cut away.

FIG. 15 is a perspective view of a sixth embodiment.

FIG. 16 is a center section view taken from FIG. 15.

FIG. 17 is a bottom view of FIG. 15 with the reservoir-handle and film cut away.

REFERENCE NUMBERS 10 applicator
12 reservoir-handle element (first element)
14 handle end
16 dispensing end
18 liquid
20 non-forming film (second element)
22 flat absorbent pad (third element)
24 weaknesses (forming a hole)
26 hand

AMENDMENTS TO THE DETAILED
DESCRIPTION OF THE INVENTION

Figure 1:
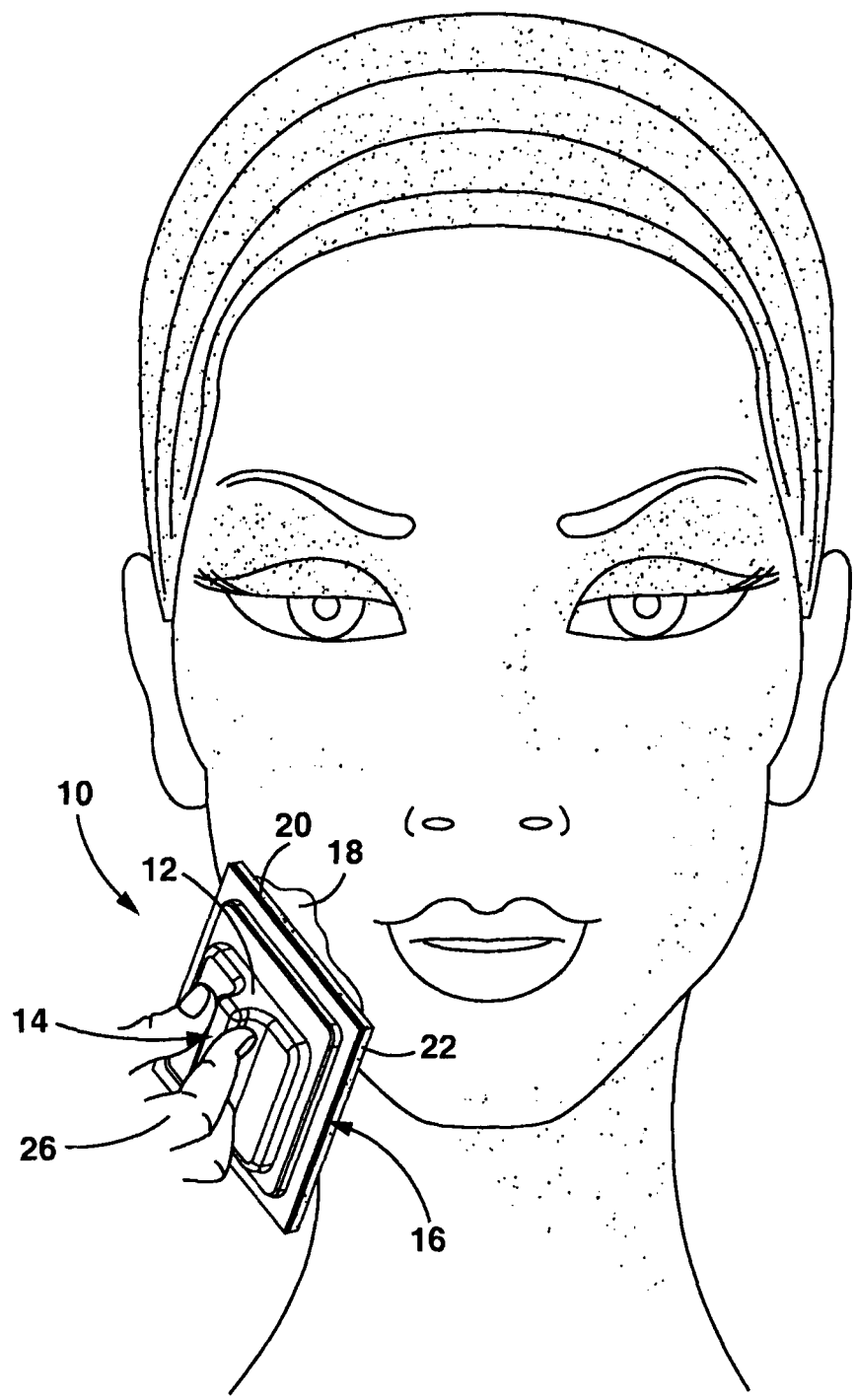
FIG. 1 is a perspective view of the Touch-Free Applicator in use.

Referring to FIG. 1, a user is holding a representative applicator 10 in her hand 26. The applicator comprises a reservoir-handle element 12 which is hollow. The reservoir-handle element comprises a closed, handle end 14 and an open, dispensing end 16. The reservoir-handle element 12 is pre-loaded with a liquid 18. An intermediate film layer 20 is sealed along the entire perimeter of the open end of the reservoir-handle element and encloses the liquid within the reservoir-handle element until it is ready to be used. This keeps the liquid free from contamination and spillage. There are frangible weaknesses (not shown in this view) built into the film layer. The user pinches a closed handle end 14 between her thumb and forefingers. The force of this pinching action pushes the liquid toward the weaknesses in the film layer, breaking the weaknesses and creating an opening through which the liquid can flow. The liquid can flow onto a flat absorbent pad 22. Note that the user is able to dispense, apply and spread the liquid in one motion without ever touching her face.

Figure 2:
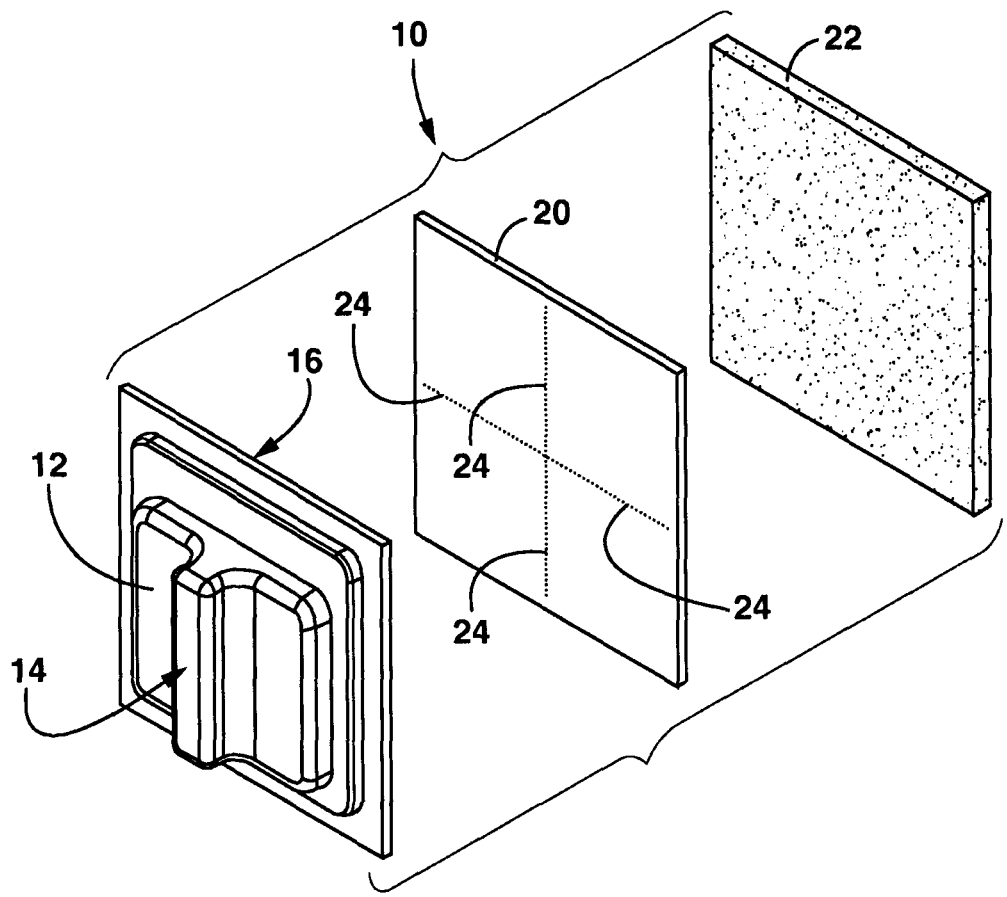
FIG. 2 is a perspective view of a typical exploded view of one embodiment of the invention.

FIG. 2 shows an exploded view of a first embodiment of the applicator 10. Note here the three layers: reservoir-handle element 12, film 20 and pad 22. The reservoir-handle element comprises a closed, handle end 14 and open, dispensing end 16, defining a hollow space. Film 20 contains micro-perforations in an X pattern. Liquid 18 fills the hollow space. Squeezing the handle end 14 forces liquid through the micro-perforations. This creates an opening through which the liquid can pass. Other sizes and patterns of micro-perforations can be determined and created by one skilled in the art, and fall within the scope of this invention. Preferably, the micro-perforations are calibrated to 0.5-1.0 burst strength. Pad 22 is absorbent for carrying the liquid held in the reservoir-handle element through to an exterior surface.

Each of these three elements is created at different stations of a form/fill/seal apparatus known in the art, then heat and vacuum sealed together as one unit. In particular, the reservoir-handle element 12 is shaped from a roll of forming film. The forming film is a co-extruded composite of two thermoplastics. The co-extruded composite shall be liquid-impermeable, sufficiently rigid to hold its own shape, yet sufficiently flexible to yield under the pressure of a user's fingers. Preferably, the co-extruded composite is selected from among: polyethylene with polypropylene, polyethylene with polyamide, polypropylene with polyamide and polyvinyl carbonate. The co-extruded composite can be colored or left colorless. Most preferably, the co-extruded composite used to form the reservoir-handle element 12 is 5 mil thick, although thicknesses of 2-12 mil fall within the scope of this invention. The thickness of the reservoir-handle element 12 can be determined by a person skilled in the art, and optimized for a particular liquid application.

The handle end 14 of the reservoir-handle element 12 can be formed from the selected material into a variety of shapes. The first embodiment is shaped like a letter T. There is a hollow central bar and arms of the T (not numbered). Liquid is pre-filled and stored in the space defined by this three-dimensional T. Ideally the user squeezes the central bar between his thumb and forefingers. The force of this pinching action pushes the liquid through the micro-perforations 24 and onto the absorbent pad 22.

In this first embodiment, the applicator is a square. However, circular, oval and other geometric shapes can also be used. The shape of the applicator can be determined by the particular use. Rounded edges are gentler on a person's skin. However, square and angled edges minimize manufacturing waste. The overall dimensions of the applicator 10 can be varied depending on the particular use. Most preferably, it is sized to fit into a user's hand, about 50.8 mm square, but other dimensions can be determined and used by one skilled in the art.

The film 20 is created from a roll of non-forming, co-extruded thermoplastic. It is impermeable to liquid. Most preferably, the non-forming thermoplastic composite is selected from the group consisting of polyethylene with biaxially oriented polypropylene, polyethylene with polyester, polyethylene with biaxially oriented nylon, polypropylene with biaxially oriented polypropylene, polypropylene with polyester and polypropylene with biaxially oriented nylon. The polyethylene and polypropylene are ideally 2 mil thick, but the thickness can be varied by those skilled in the art to optimize the storage and tearing requirements of a particular liquid. The biaxially oriented polypropylene, biaxially oriented nylon and polyester are ideally 50 gauge, but other gauges can be used to optimize the storage and tearing requirements of a particular liquid.

The film 20 has a perimeter. In this embodiment, it is square. The film is cut to the same dimensions as the handle/reservoir element. In each unit of this embodiment, the film bears a pattern of pre-formed micro-perforations. Preferably the micro-perforations are 1-3 mm apart. Most preferably, they are 1 mm apart. Most preferably, the micro-perforations are calibrated to a burst strength of 0.5-1 psi. Preferably, the pattern forms an X. The X pattern, when torn, creates a large opening through which liquid can flow. However, other sizes and patterns fall within the scope of this invention and can be selected to optimize the flow of liquid. The micro-perforations are small enough and far enough apart to retain liquid within the reservoir-handle while the applicator is in storage, yet close enough together to open under pressure.

The absorbent pad 22 is cut to the same perimeter as both the reservoir-handle element 12 and the film 20. In the first embodiment, this is a square approximately 50.8 mm on each side. Most preferably, the pad is made from a material selected from among: polyester, polyester blended with regenerated cellulose fiber, polypropylene blended with cellulose pulp, and cotton. The thickness of the absorbent pad varies, but most preferably is 0.2-2.5 mm, or 30-65 gsm. Other thicknesses may be selected without deviating from the scope of this invention. All three layers are sealed into a single unit. In all embodiments, there is a flange (not numbered) formed when the layers are sealed. In this representative embodiment, this flange is 6.5 mm, but other dimensions can be used without deviating from the spirit of this invention.

To assemble the applicators, a roll of reservoir-handle material is loaded onto one station of a form/fill/seal apparatus. The reservoir-handle material is unrolled into a sheet and pressed into the desired three-dimensional shape. This embodiment shows a T-shaped handle. From a single sheet, the apparatus presses multiple rows and columns of joined reservoir-handle material. This sheet of joined reservoir-handles indexes to a second station, where each reservoir is filled with a pre-measured amount of liquid. The roll further indexes to a third station, where a roll of film awaits. The roll of film is laid over the sheet of filled reservoir-handles and heat and pressure sealed. The liquid is thereby enclosed. The composite reservoir-handle and film sheet then travels to a fourth station, where a roll of absorbent pad material awaits. The apparatus unrolls the absorbent pad into a sheet and lays it atop the film side of the reservoir-handle/film composite. The three layers then travel as a single sheet to a fifth station where the pad is heat and pressure sealed to the film side of the composite. Finally, the three-layer composite applicator indexes to a sixth station where it is slit and cut into individual units.

In this first embodiment, the roll of non-forming film has already been micro-perforated. A laser creates micro-perforations at regular intervals along the width and the length of the roll, such that aligning an end length of the reservoir-handle film with an end length of the non-forming film positions the micro-perforation pattern precisely in the center of each applicator unit. The micro-perforations are preferably calibrated to a burst strength of 0.5-1.0 psi.

FIG. 3, FIG. 4 and FIG. 5 show in three different perspectives a second embodiment of the invention. Externally the second embodiment appears identical to the first embodiment. There is the same reservoir-handle element 12, intermediate film layer 20 and absorbent pad 22. The hollow space defined by the closed, handle end 14 and open, dispensing end 16 is filled with a liquid 18. The liquid is sealed inside the reservoir-handle with a layer of film 20. However, in this embodiment, the sheet of film 20 has no micro-perforations. Rather, there is a pair of U-shaped lines 24 of differential sealing (shown in dark dashes). An end of a sheet of unperforated film 20 is aligned against a corresponding end of a reservoir-handle and sealed in two steps. The form/fill/seal apparatus seals the two layers around approximately ⅞ of the perimeter with a first pressure. Then it seals a remaining ⅛ of the edge with a weaker seal, in a U-shaped line 24 (shown). Multiple rows and columns of applicator units are formed and sealed in unison. These U-shaped lines show where the reservoir-handle is more weakly sealed to the film. Pinching the handle 14 forces the liquid 18 against weaker seals 24. Using 0.5-1 psi of pressure, these inner seals will break, but the perimeter seals will not break. This creates a passageway for the liquid form the reservoir-handle and onto the pad.

Figure 6:
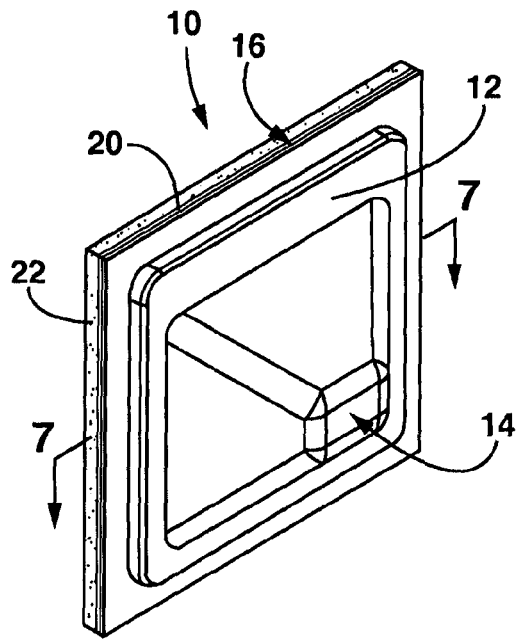
FIG. 6 is a perspective view of a third embodiment.
Figure 7:
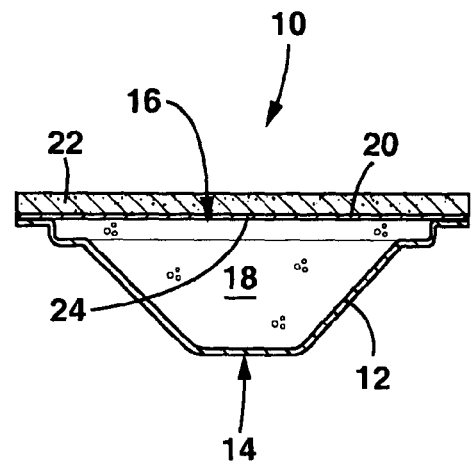
FIG. 7 is a center section view taken from FIG. 6.
Figure 8:
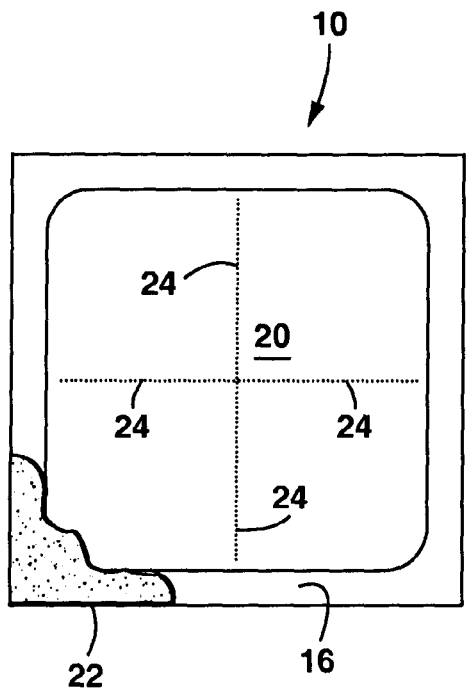
FIG. 8 is a bottom view of FIG. 6 with the reservoir-handle and film cut away.

FIG. 6, FIG. 7 and FIG. 8 show three perspective views of a third embodiment. Note here the square profile and micro-perforations 24 as in the first embodiment. However, this embodiment has a handle end 14 in the shape of a truncated pyramid. Most preferably, in a 50.8 mm square applicator, the height of the pyramid is 14 mm. However, other dimensions and proportions may be used which still fall within the purview of this invention. In practice, the user squeezes any two opposite sides of the pyramid between the thumb and forefinger. The force of pinching drives liquid toward the micro-perforations, tearing them apart to create a hole large enough for liquid to pass. The size and pattern of micro-perforations can be varied by those skilled in the art to suit a particular liquid or use.

FIG. 9, FIG. 10 and FIG. 11 show three perspective views of a fourth embodiment. The fourth embodiment uses the same differential seal dispensing mechanism and the same T-shaped handle as the second embodiment. The circle is most preferably 50.4 mm in diameter, but can be varied by those skilled in the art, without any undue experimentation.

FIG. 12, FIG. 13 and FIG. 14 show three perspective views of a fifth embodiment. This embodiment illustrates a third handle style 14 wherein a pair of indentations suggests where a user should place a thumb and forefinger for optimum pinching power. There are micro-perforations and a circular profile as in the fourth embodiment. The circle is most preferably 50.4 mm in diameter, but can be varied by those skilled in the art, without any undue experimentation.

FIG. 15, FIG. 16 and FIG. 17 show three perspective views of a sixth embodiment. This embodiment illustrates a fourth handle style 14, in the shape of a truncated cone. In practice, a user places a thumb and forefinger on any diametrically opposite sides of the cone and squeezes. There are micro-perforations and a circular profile as in the fourth and fifth embodiments. The circle is most preferably 50.4 mm in diameter, but can be varied by those skilled in the art, without any undue experimentation.

Figure 18:
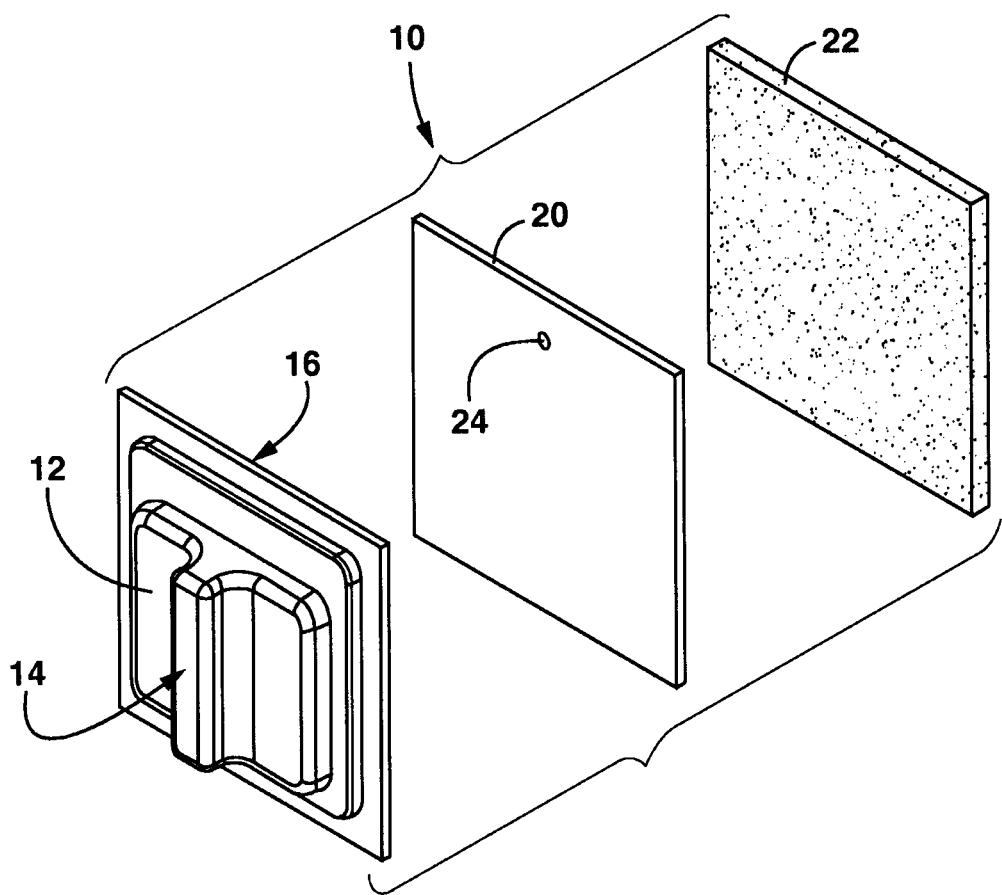
FIG. 18 is a perspective view of a typical exploded view of a seventh embodiment of the invention.

FIG. 18 shows an exploded view of a seventh embodiment of the invention. The frangible element 24 of this embodiment comprises a simple hole in the non-forming film. The user squeezes handle 14 gently to dispense liquid onto pad 22.

Figure 19:
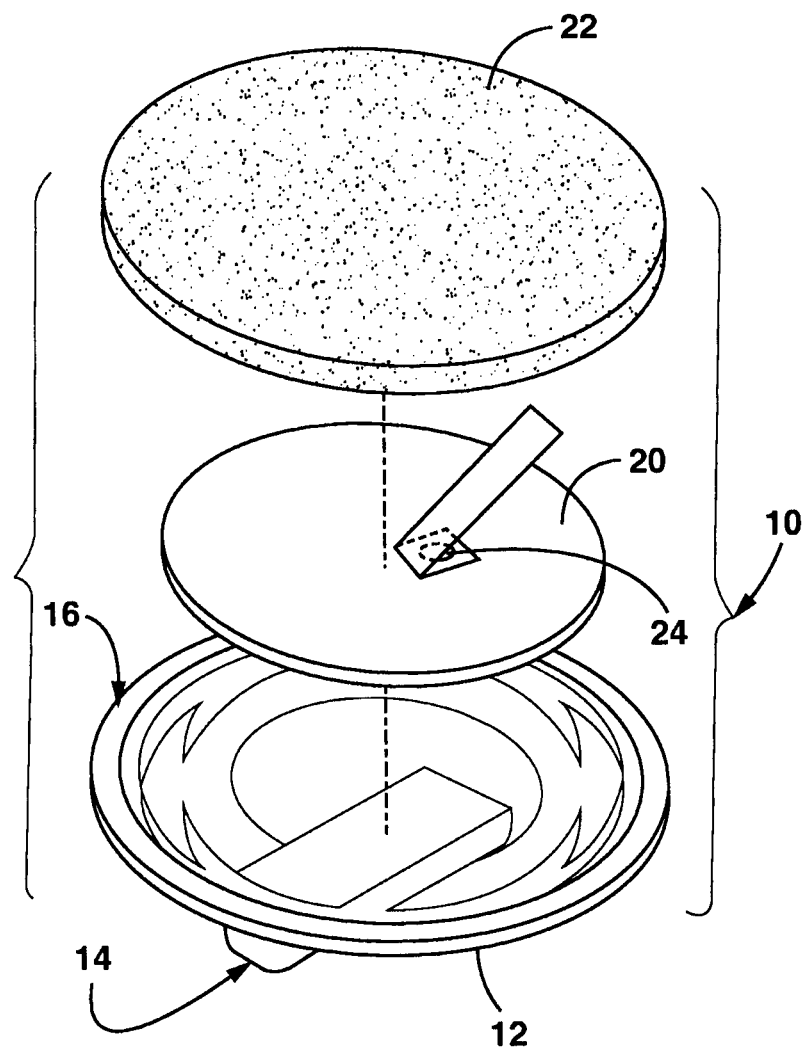
FIG. 19 is a perspective view of a typical exploded view of an eighth embodiment of the invention.

FIG. 19 shows an exploded view of an eighth embodiment of the invention. The frangible element 24 in this embodiment comprises a simple hole in the non-forming film, completely covered with a tab (not numbered). A portion of this tab extends beyond the perimeter of the applicator. A user pulls the tab away from the applicator to expose the hole within the applicator. Liquid in the reservoir flows through the hole and onto the pad 22 as in the other embodiments.

The invention claimed is:

1. A unitary touch-free liquid applicator comprising a/an:
   a. reservoir-handle element comprising a composite forming web consisting of at least two distinct co-extruded thermoplastic materials, this reservoir-handle element having a handle end and an opposing open, dispensing end, such that the boundary of the handle end with the dispensing end defines a perimeter,
   b. film element comprising a composite non-forming web consisting of at least two distinct co-extruded thermoplastic materials, said film securely sealed in a first seal to the perimeter of the dispensing end of the reservoir-handle element, said film bearing frangible weaknesses within the area bound by the sealed perimeter, and
   c. absorbent pad securely sealed in a second seal to the same perimeter on a side of the film not sealed to the reservoir-handle, such that
   d. squeezing the reservoir-handle element with sufficient force drives a liquid through the frangible weaknesses in the film and onto the absorbent pad.

2. A unitary liquid applicator as in claim 1, wherein the reservoir-handle element bears surface details suggesting where to optimally place a user's thumb and forefingers.

3. A unitary liquid applicator as in claim 1, wherein the thermoplastic materials to be co-extruded into the composite forming web are selected from the group consisting of: polyethylene, polypropylene, polyamide, and polyvinyl carbonate.

4. A unitary liquid applicator as in claim 3, wherein the composite co-extruded forming web has a total thickness of 2-12 mil.

5. A unitary liquid applicator as in claim 4, wherein the composite co-extruded forming web has a total thickness of 5 mil.

6. A unitary liquid applicator as in claim 1, wherein the thermoplastic materials to be co-extruded into the composite non-forming film are selected from the group consisting of: polyethylene, polypropylene, biaxially oriented polypropylene, polyester, polyamide, biaxially oriented polyamide, and biaxially oriented nylon.

7. A unitary liquid applicator as in claim 6, wherein the polyethylene, if chosen, has a thickness of 2-8 mil, the polypropylene, if chosen, has a thickness of 2-8 mil, the biaxially oriented polypropylene, if chosen, has a gauge of 30-50, the polyester, if chosen, has a gauge of 30-50 and the biaxially oriented polyamide, if chosen, has a gauge of 30-50.

8. A unitary liquid applicator as in claim 1, wherein the frangible weaknesses in the film comprise a set of micro-perforations created in the film.

9. A unitary liquid applicator as in claim 1, wherein the frangible weaknesses in the film comprise an third, inner seal within the bounds of the sealed perimeter, this third inner seal being weaker than the seal joining the perimeter of the reservoir-handle to the corresponding perimeter of the film.

10. A unitary liquid applicator as in claim 1, wherein the frangible weaknesses in the film comprise a hole in the non-forming film and also a pull tab covering this hole and extending through and beyond the perimeter.

11. A unitary liquid applicator as in claim 1, wherein the absorbent pad is formed from a material selected from the group consisting of: polyester, polyester blended with regenerated cellulose fiber, polypropylene blended with cellulose pulp, and cotton.

12. A method of making a unitary touch-free applicator, comprising:
 a. providing a forming web comprised of a composite of at least two distinct co-extruded thermoplastic materials;
 b. providing a non-forming film comprised of a composite of at least two distinct co-extruded thermoplastic materials;
 c. providing an absorbent pad;
 d. shaping the composite thermoplastic forming web into a hollow reservoir-handle element, wherein the hollow reservoir-handle element has a closed, handle end and an opposing open, dispensing end, such that the boundary of the handle end with the dispensing end defines a perimeter;
 e. filling the hollow reservoir-handle element with a liquid;
 f. creating frangible weaknesses in the non-forming thermoplastic film;
 g. sealing in a first seal the perimeter of the open end of the reservoir-handle to the non-forming thermoplastic film, thereby enclosing the liquid between one side of the non-forming web and the closed end of the reservoir-handle;
 h. sealing the absorbent pad to the side of the non-forming thermoplastic film not facing the liquid, this second seal being created along the same perimeter as the first seal.

13. The method of claim 12, wherein the thermoplastic materials to be co-extruded into the composite forming web are selected from the group consisting of: polyethylene, polypropylene, polyamide, and polyvinyl carbonate.

14. The method of claim 12, wherein the thermoplastic materials to be co-extruded into the composite non-forming film are selected from the group consisting of: polyethylene, polypropylene, biaxially oriented polypropylene, polyester, polyamide, biaxially oriented polyamide, and biaxially oriented nylon.

15. The method of claim 12, wherein creating the frangible weaknesses comprises micro-perforating the film.

16. The method of claim 12, wherein creating the frangible weaknesses comprises creating a third, inner seal within the bounds of the second seal, this third inner seal being weaker than the second seal joining the perimeter of the reservoir-handle to the corresponding perimeter of the film.

17. The method of claim 12, wherein creating the frangible weaknesses comprises punching a hole in the film and also covering this hole with a pull tab extending through and beyond the perimeter.

18. The method of claim 12, wherein the absorbent pad is formed from a material selected from the group consisting of: polyester, polyester blended with regenerated cellulose fiber, polypropylene blended with cellulose pulp, and cotton.

* * * * *